United States Patent [19]

Streicher

[11] Patent Number: 5,607,557
[45] Date of Patent: Mar. 4, 1997

[54] ETHYL TERTIO-BUTYL ETHER PURIFICATION PROCESS COMBINING A MEMBRANE METHOD AND DISTILLATION

[75] Inventor: Christian Streicher, Rueil Malmaison, France

[73] Assignee: Institut Francais du Petrole, Rueil-Malmaison, France

[21] Appl. No.: 411,519

[22] Filed: Mar. 28, 1995

[30] Foreign Application Priority Data

Mar. 28, 1994 [FR] France .................... 94 03606

[51] Int. Cl.$^6$ .............. B01D 3/00; C07C 41/42
[52] U.S. Cl. ............ 203/39; 203/94; 203/98; 203/99; 203/DIG. 9; 203/DIG. 19; 203/DIG. 16; 210/500.27; 210/500.35; 210/640; 210/649; 568/697; 568/699; 568/913
[58] Field of Search ............ 203/39, 99, DIG. 16, 203/14, 18, 43, DIG. 13, DIG. 19, 94, 98, DIG. 9; 568/697, 699, 913; 159/DIG. 27, DIG. 28; 210/500.27, 500.35, 640, 649

[56] References Cited

U.S. PATENT DOCUMENTS

| 4,728,429 | 3/1988 | Cabasso et al. .......... 210/640 |
| 4,774,365 | 9/1988 | Chen et al. ............... 568/697 |
| 4,925,562 | 5/1990 | te Hennepe et al. ...... 210/640 |
| 4,978,430 | 12/1990 | Nakagawa et al. ....... 159/DIG. 27 |
| 5,146,009 | 9/1992 | Cohen et al. ............. 568/889 |
| 5,147,549 | 9/1992 | Chou et al. .............. 210/640 |
| 5,158,652 | 10/1992 | Pucci et al. ............... 203/73 |
| 5,250,156 | 10/1993 | Pucci et al. ............... 203/73 |
| 5,292,963 | 3/1994 | Kanji et al. ............... 568/697 |
| 5,294,344 | 3/1994 | Feimer et al. ............. 210/640 |
| 5,348,624 | 9/1994 | Pucci et al. ............... 203/77 |
| 5,401,887 | 3/1995 | Rastelli et al. ............ 568/697 |

FOREIGN PATENT DOCUMENTS

| 0331846A3 | 9/1989 | European Pat. Off. . |
| 0497680A1 | 8/1992 | European Pat. Off. . |
| 0507076A1 | 10/1992 | European Pat. Off. . |
| 0542596A1 | 5/1993 | European Pat. Off. . |

Primary Examiner—Virginia Manoharan
Attorney, Agent, or Firm—Pollock, Vande Sande & Priddy

[57] ABSTRACT

A process for separating a mixture containing mainly ethyl tertio-butyl ether (ETBE), ethanol and $C_4$ hydrocarbons includes introducing the mixture to be separated into a debutanizer from which the $C_4$ hydrocarbons are recovered overhead with a fraction of the ethanol, and purified ETBE is recovered as a bottom product; a side stream of an ethanol-rich phase is extracted and sent to a permeation zone in which the dense film of the membrane is constituted by a N,N-dimethylaminoethyl methacrylate polymer (DMAEMA) or a copolymer of DMAEMA with N-vinyl-caprolactam (NVCL) and/or with N-vinyl pyrrolidone (NVP); the ethanol-depleted retentate from this permeation zone is returned to the debutanizer and the permeate contains mainly separated ethanol.

The process can be integrated into an ETBE production process, in which the ethanol separated during the permeation step is recycled to the etherification reactor. The debutanizer may be replaced by a catalytic distillation column.

17 Claims, 1 Drawing Sheet

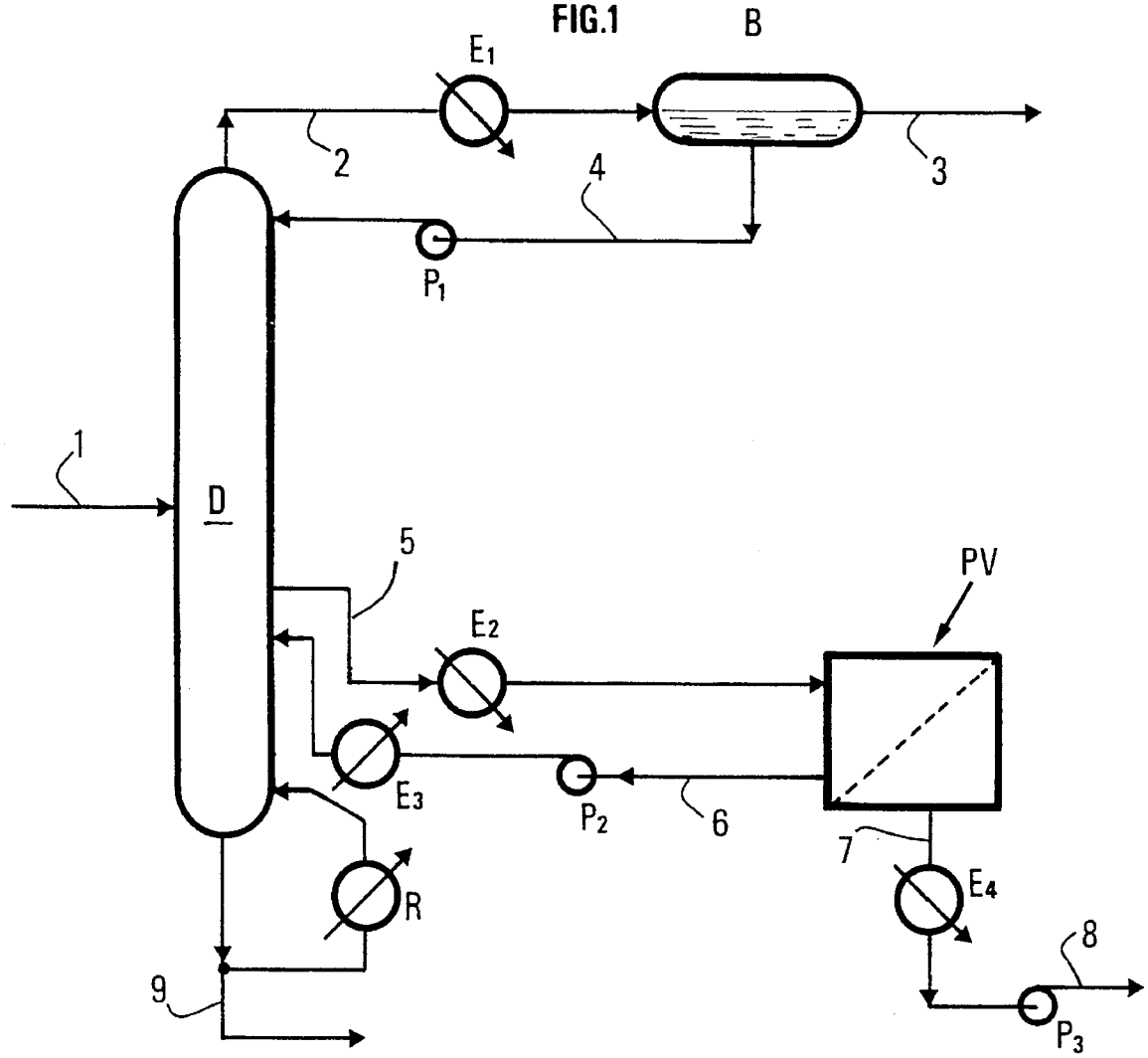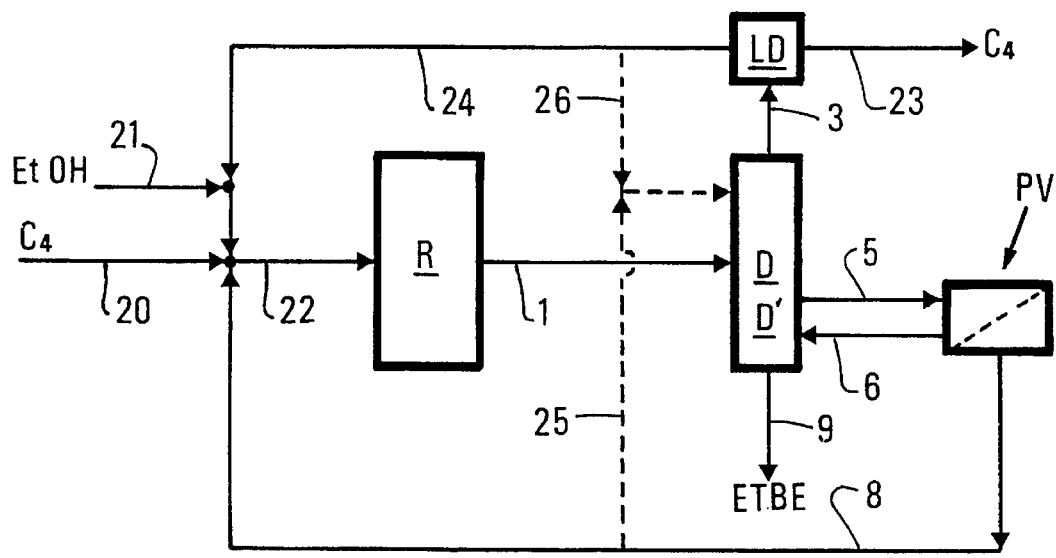

5,607,557

ETHYL TERTIO-BUTYL ETHER PURIFICATION PROCESS COMBINING A MEMBRANE METHOD AND DISTILLATION

FIELD OF THE INVENTION

The invention concerns the production of ethyl tertio-butyl ether (ETBE).

STATE OF THE ART

Ethyl tertio-butyl ether, like methyl tertio-butyl ether (MTBE) can be used as a high octane number additive for unleaded or low lead petrols. ETBE can be added to petrols in concentrations of up to about 15% by volume, for example.

One production process for MTBE consists in carrying out an addition reaction between methanol and isobutene, contained for example in a $C_4$ cut from steam cracking or catalytic cracking. After reaction, the residual methanol is usually separated by azeotropic distillation with $C_4$ hydrocarbons and MTBE is readily obtained with a degree of purity which is suitable for addition to petrols.

ETBE can be produced using an analogous process in which ethanol replaces methanol. An example of this process is described in "ETBE, un avenir pour l'ethanol" (translation: ETBE, a future for ethanol), by A Forestiere, B Torck and G Pluche, given at the Conference sur la Biomasse pour l'Energie et l'Industrie, Lisbon, 9–13 Oct. 1989, and in "MTBE/ETBE, an incentive Flexibility for Refiners" by A Forestiere et al., given at the "Conference on Oxygenated Fuels in Europe", London, 22–23 May 1990.

Contrary to the case of MTBE, however, after eliminating the $C_4$ hydrocarbons by azeotropic distillation (debutanizer) in this process, almost all the residual ethanol is mixed with the ETBE product at the bottom of the debutanizer. The existence of an ethanol-ETBE azeotrope with 21% by weight of ethanol at atmospheric pressure, which boils at 66.6° C., makes it difficult to separate the ETBE with an adequate purity to satisfy regulations regarding concentrations of ethanol in petrol. Thus the ethanol content in ETBE must in general be between 0.1% and 10% by weight. Advantageously, the ETBE should be purified to less than 1% by weight of ethanol for it to be able to be added to petrol.

Thus, in order for ETBE to compete with MTBE as an additive which improves the octane number in unleaded petrol, the development of an economically attractive separation process would be particularly desirable.

A number of processes have been described for purifying the ETBE obtained from the bottom of the debutanizer.

French patent FR-B-2 683 523 describes a process in which the alcohol/ETBE mixture obtained from the bottom of the debutanizer is washed with water and the water/alcohol mixture obtained is concentrated in a first distillation column then dehydrated in two further heteroazeotropic distillation columns using ETBE as the azeotroping agent. This process, however, is relatively complex and costly since it requires the use of 4 columns (1 washing column, 1 concentration column and 2 heteroazeotropic distillation columns). There is the additional drawback of producing water-saturated ETBE which is not of advantage as regards its use as an additive for petrol.

A simpler separation process for ethanol/ETBE mixtures has been described in French patent FR-B-2 672 048.

This process exploits the change in the composition of the azeotropic ethanol/ETBE mixture with pressure. The ethanol/ETBE mixture is thus separated using two distillation columns operating at two different pressures. Pure ETBE is thus obtained from the bottom of the first column operating at high pressure and pure ethanol is obtained from the bottom of the second column operating at low pressure. The azeotropic mixtures obtained overhead from each column are recycled to the other column.

French patent FR-B-2 673 624 describes a separation process for ethanol/ETBE mixtures by heteroazeotropic distillation using water as the azeotroping agent. Again, this process uses two distillation columns which can be operated at two different pressures and which respectively produce ethanol and pure ETBE at the bottom of each in analogous fashion to the process described above.

These two processes, however, require the use of two distillation columns which renders these processes relatively expensive as regards both investment and energy consumption. Further, as mentioned in French patent FR-B-2 672 048, the ethanol/ETBE mixtures obtained from the bottom of the debutanizer in ETBE synthesizing processes contain other impurities such as tertiary-butyl alcohol (TBA), diethyl ether (DEE), $C_5$ hydrocarbons ($C_5$), and ethyl 2-butyl ether (E2BE). Some of these impurities (DEE, $C_5$) are taken overhead from these distillation columns in the processes described in FR-B-2 672 048 and FR-B-2 673 624. Since the overhead products are completely recycled in these processes, these impurities accumulate gradually until they disturb the operation of the process and degrade the quality of separation, necessitating a purge overhead of one or other column to overcome this problem.

United States patent U.S. Pat. No. 4,774,365 describes a process combining the step of azeotropic distillation (debutaniser) with a pervaporation step which produces an ether which is free of alcohol from the bottom of the azeotropic distillation column.

In a first embodiment of the process, the effluent from the reaction section passes over a pervaporation membrane which is selectively permeable to alcohol. The retentate produced from the pervaporation step is thus depleted in alcohol. It is then distilled in a column which produces ether from the bottom and the hydrocarbons present in the effluent from the reaction section overhead. When the alcohol used to synthesize the ether is methanol as is the case, for example, for MTBE or tertio-amyl methyl ether (TAME), the residual methanol which is not extracted during the pervaporation step is recovered overhead of the distillation column with the hydrocarbons. This process is thus highly suitable for the production of methanol-free ethers. However, if this process is attempted for the purification of ETBE as already indicated a major proportion of the ethanol is recovered from the bottom of the debutanizer with the ETBE. This process, then, could only produce ethanol-free ETBE if all the ethanol present in the effluent from the reaction section at the pervaporation step could be extracted. However, like all other membrane processes, pervaporation alone cannot produce very pure products economically; thus in this case, extraction of the last traces of ethanol from the retentate, even with a high performance membrane, would mean the use of economically unrealistic membrane surfaces. Thus this embodiment in U.S. Pat. No. 4,774,365 cannot economically produce ethanol-free ETBE.

In another embodiment in the same patent, the effluent from the reaction section is introduced directly into the azeotropic distillation column. A liquid fraction is extracted from this column as a side stream, then sent to a pervaporation step which selectively extracts a portion of the alcohol. The alcohol-depleted retentate produced by this pervaporation step is then recycled to the azeotropic distillation column. This embodiment can produce ETBE from the bottom of the debutanizer with an ethanol content of less than 1% by weight, and even less than 0.1% by weight, provided that a membrane is used which can selectively extract ethanol from a mixture of ethanol/ETBE, and hydrocarbons. However, U.S. Pat. No. 4,774,365 only mentions the existence of membranes which can selectively extract methanol and the description of the process described in that patent only mentions its use for the purification of MTBE and TAME.

To date, a small number of publications have described membranes which can selectively extract ethanol from organic mixtures: see, for example, U.S. Pat. Nos. 4,547,530 and 5,066,403.

The membranes described in these documents, however, do not have suitable performance characteristics (permeability, selectivity, thermal stability) to enable them to be used industrially. In addition, these membranes cannot be used to selectively extract alcohols containing more than three carbon atoms. Further, as seen above, during the synthesis of ETBE, a certain amount of TBA is formed by addition of one molecule of water to one molecule of isobutene. The presence of water in the reaction section is inevitable, as it has been introduced as an impurity in the products supplied to said reaction section ($C_4$ cut, ethanol), and it is also formed in the reaction section itself by the unavoidable secondary reaction of etherifcation of ethanol during which two molecules of ethanol form one molecule of DEE and one molecule of water. Since the reaction which produces TBA is thermodynamically balanced, separating the TBA from the ETBE product at the bottom of the debutanizer and recycling the TBA to the reaction section limits the conversion of isobutene to TBA and thus increases the conversion of isobutene to ETBE. It is thus particularly desirable to develop a process which will enable simultaneous separation of alcohols (ethanol/TBA) from ETBE so that the alcohols can be recycled to the reaction section in a simpler and more economical fashion than that of the distillation processes described in the French patents cited above.

OBJECT OF THE INVENTION

The present invention thus relates to a process for the purification of ETBE combining an azeotropic distillation step (debutanizer), normally present after the reaction section in ETBE synthesis processes, with a permeation step, to obtain ETBE from the bottom of the debutaniser which is practically free of the alcohols (ethanol, TBA) present in the effluent from the reaction section. The ETBE obtained can contain less than 1% by weight, or even less than 0.1% by weight of residual alcohols.

The process of the present invention is also applicable when the azeotropic distillation step is constituted by a conventional distillation column (debutanizer) when this is a catalytic or reactive distillation step such as that described in "La distillation reactive: principe, applications et perspectives" (translation: Reactive Distillation: Principles, Applications and Perspectives), P Mikitenko, published in P étrole et techniques, no. 329, December 1986, p 34–38.

The present invention also relates to a process for the synthesis of ETBE including the ETBE purification process of the present invention, in which the alcohols extracted during the permeation step are recycled to the reaction section or optionally to the catalytic or reactive distillation step when such a process is employed.

The process of the present invention is particularly applicable to mixtures of ETBE, ethanol and $C_4$ hydrocarbons which constitutes the effluents from the reaction sections from ETBE synthesis processes.

These mixtures generally contain 0.1% to 20% by weight, preferably 0.5% to 5% by weight, of ethanol and 5% to 80% by weight, preferably 10% to 50% by weight of ETBE, the remainder being mainly constituted by hydrocarbons containing 4 carbon atoms, $C_4$: n-butane, isobutane, butenes and unreacted isobutene. They also generally contain, as impurities, up to 1% by weight of water, up to 1% by weight of TBA, up to 1% by weight of DEE, up to 1% by weight of secondary butyl ethyl ether (E2BE), up to 5% by weight, preferably less than 1% by weight, of hydrocarbons containing 5 carbon atoms, $C_5$: pentanes and pentenes, and up to 5% by weight of hydrocarbons containing 3 carbon atoms, $C_3$: propane, propylene.

DESCRIPTION OF THE INVENTION

The mixture to be separated is introduced into the debutanizer. The debutanizer is operated at a pressure which is generally above atmospheric pressure, preferably between 5 and 15 bar. A distillate containing most of the $C_3$, $C_4$ and water from the mixture to be separated, and a fraction of the ethanol and $C_5$ from the mixture to be separated, the distillate being substantially free of other compounds (ETBE, E2BE, TBA, DEE), is recovered overhead. The majority of the ETBE and the other ethers (E2BE, DEE), along with a fraction of the $C_5$ and small amounts (less than 1% by weight, preferably less than 0.1% by weight) of alcohols (ethanol, TBA) are recovered from the bottom of the debutanizer.

At least one liquid, vapor or mixed phase is extracted as a side stream from the debutanizer and sent to a permeation zone.

The term permeation zone here means a pervaporation zone when a liquid phase is brought into contact with the upstream face of the membrane or a vapor permeation zone when using a gaseous or mixed phase.

According to one feature of the process, at least one phase is extracted as a side stream from at least one tray of the debutanizer where the ethanol concentration is substantially at a maximum.

In accordance with a further feature of the process, The permeation zone is provided with a composite membrane which is normally constituted by a selective layer deposited on at least one porous support layer. While the support layer(s) can be constituted by any type of organic or inorganic material which is normally used to form membrane supports, the selective layer itself is a characteristic of the process of the present invention and is constituted by a dense film of a homo-, co- or terpolymer. The homopolymer used is poly N,N-dimethylaminoethyl methacrylate (DMAEMA). The copolymer can be constituted by DMAEMA and N-vinylcaprolactam (NVCL) or by DMAEMA and N-vinyl pyrrolidone (NVP), and the terpolymer is constituted by DMAEMA, NVCL and NVP. The amine group of the DMAEMA is preferably quaternized to a quaternary ammonium group. Preferred quaternization reactants are dimethyl and diethyl sulphate, also monochloro-, monobromo- or monoiodo-methane or ethane. After depositing the selective layer on the support layer(s) by coating, the membrane formed is heat treated at temperatures of 100° C. to 200° C. for periods of 1 to 60 minutes to render the selective layer insoluble in water alcohols and organic solvents. This selective layer has the advantage of being selectively permeable to alcohols, not only to ethanol, but also to other alcohols, in particular TBA. Thus the compounds from the extracted phase(s) can also be extracted.

In accordance with a further feature of the process, the phase(s) extracted from the debutanizer is/are admitted into the permeation zone at a temperature and pressure which can be greater or less than when extracted. The optional changes in temperature and pressure can be carried out using suitable equipment (pumps, compressors, pressure reduction valves, exchangers).

In accordance with another feature of the process, the alcohol-depleted retentate which has not passed through the membrane can be recycled to the distillation zone. This retentate can be obtained after the permeation zone in a liquid, gaseous or mixed phase. In order to be recycled to the distillation zone, it must be brought to a pressure at least equal to that of said distillation zone, using suitable equipment (pumps, compressors). It can also be brought to a temperature which is greater than or less than that at which it is recovered after the permeation zone using appropriate equipment, (exchangers). The phase(s) which are thus recycled to the distillation zone is/are advantageously recycled to tray(s) where the composition is substantially the same as that of said recycled phase(s).

Finally, a permeate constituted mainly by alcohols (ethanol, TBA), is recovered downstream of the permeation membrane and advantageously recycled to the reaction zone.

BRIEF DESCRIPTION OF DRAWINGS

FIGS. 1 and 2 illustrate apparatus suitable for carrying out the process of the present invention.

BEST AND VARIOUS MODES FOR CARRYING OUT INVENTION

An advantageous embodiment of the invention will now be described with reference to FIG. 1.

The mixture to be separated is sent via line 1 to distillation column D (debutanizer). This column generally operates at a pressure p greater than 1 bar, preferably between 5 and 15 bar. It is heated by reboiler R. The bottom temperature is generally between 70° C. and 200° C. The top temperature is generally between 30° C. and 100° C. The mixture to be separated is preferably introduced into debutanizer D at the bubble point at the pressure used to the tray with the closest composition possible to that of the mixture, for example to the central portion of the column in the case of mixtures containing 10% to 50% by weight of ETBE.

The product leaving the bottom of the debutaniser via line 9 is constituted by purified ETBE. Almost all of the ethers present in the mixture to be separated, ETBE and also E2BE and DEE, are thus recovered practically free of $C_3$, $C_4$ and water, with a $C_5$ content which depends on that of the mixture to be separated, generally between 0.1% and 1% by weight, and with residual amounts of alcohols (ethanol and TBA) which depend on the operating conditions of the process, and are less than 1% by weight and even less than 0.1% by weight.

A vapour phase distillate constituted by $C_3$, $C_4$ and $C_5$ hydrocarbons is recovered from the debutanizer via line 2. It contains a variable proportion of ethanol, generally between 1% and 5% by weight, along with water at a concentration generally of less than 1% by weight and is practically free of TBA and ethers (ETBE, E2BE, DEE).

This vapour phase is completely condensed and optionally undercooled in exchanger. E1 then admitted into drum separator B. From drum B, a liquid distillate is recovered via line 3 which has the same composition and contains almost all the water and the $C_3$ and $C_4$ hydrocarbons from the mixture to be separated. The remainder of the liquid recovered from drum B is sent via line 4 by means of pump P1, as a reflux to the top of debutanizer D.

A fraction which is preferably liquid is removed via line 5 as a side stream from debutanizer D. This side stream is preferably extracted from the tray where the ethanol concentration in the liquid phase is at a maximum, in general at a tray which is lower than that at which the mixture to be separated is supplied to debutaniser D. The mass flow rate of the removed fraction is an important operating parameter of the process. It must be adjusted as a function of the other operating parameters and the residual alcohol (ethanol, TBA) content required in the ETBE recovered from the bottom of debutanizer D.

In exchanger E2, the liquid fraction extracted as a side stream is brought to a temperature which is generally between 50° C. and 120° C., preferably between 80° C. and 100° C., then introduced into the pervaporation zone PV.

The pervaporation zone PV is provided with a membrane comprising a dense selective layer constituted by a homo-, co- or terpolymer, the homopolymer being DMAEMA, the copolymers being constituted by DMAEMA and NVCL or DMAEMA and NVP, and the terpolymer being constituted by DMAEMA, NVCL and NVP the material which is preferably used being a copolymer of NVP and DMAEMA, the amine group of the DMAEMA being preferably quaternized to a quaternary ammonium group by reaction with dimethyl or diethyl sulphate or monochloro-, monobromo- or monoiodo-methane or ethane.

If the respective molar fractions of DMAEMA, NVP and NVCL are designated as x, y and z and normalised so that: x+y+z=1; x can be between 1 (homopolymer) and 0.1: y and z can each be between 0 and 0.9. For copolymers (y=0 or z=0), values for x of between 0.2 and 0.8 are preferred, in particular between 0.4 and 0.6. For terpolymers, values for x, y and z each of between 0.2 and 0.5 are preferred.

The average molecular weight of the homo-, co- or terpolymers can be between 50 000 and 5 000 000 Dalton, preferably between 100 000 and 1 000 000 Dalton.

The dense selective layer is formed by spreading a solution of the polymer in water, ethanol or mixtures thereof onto a support. The solution can contain 2% to 50% by weight of polymer, preferably 4% to 20% by weight. After evaporating the solvent from the spread solution, at temperatures of less than 100° C., the membrane obtained is heat treated at temperatures between 100° C. and 200° C., preferably between 120° C. and 160° C., for a period of between 1 and 60 minutes. The heat treatment is preferably effected in two steps: a first step of 1 to 30 minutes duration, for example, at a temperature of between 100° C. and 120° C., for example 100° C.; and a second step, for example of 1 to 30 minutes duration, at a temperature of between 110° C. and 200° C., for example 140° C.

The thickness of the dense selective layer obtained depends on the viscosity of the polymer solution and on the method of spreading. It is preferably between 0.5 and 20 μm, more preferably between 1 and 5 μm.

While the membrane used in pervaporation zone PV can be constituted by said dense selective layer alone, it is preferably constituted by a composite structure in which the dense selective layer is formed by coating the polymer solution onto the surface of a porous structure which is preferably constituted by:

a base which is preferably constituted by a woven or non woven sheet formed from fibres of organic materials such as polyethylenes, polypropylenes, polyamides, polyesters, polyphenylene sulphides and other similar materials, or from fibres of inorganic materials such as carbon or glass; said base can also be constituted by a porous ceramic body;

a porous support layer on which the dense selective layer is deposited, having an asymmetrical structure, deposited on the base and preferably constituted by organic materials such as polysulphones, polyolefins, polyacrylonitriles, polyamides and other similar materials: the porous support layer can also be constituted by inorganic materials such as ceramics.

Pervaporation unit PV produces an alcohol-depleted retentate (ethanol, TBA) via line 6. Pump P2 brings the retentate to a suitable pressure to be returned to debutanizer D. The retentate can be reheated and optionally at least partially vaporized in exchanger E3 before being returned to debutanizer D. The retentate is preferably recycled to debutaniser D at the bubble point for that particular pressure, to the tray at which the liquid composition is the closest to that of the retentate, generally to a tray which is lower than that from which the side stream is extracted.

In the case where the retentate is at least partially vaporized before being recycled to debutanizer D it can be advantageous, after separating the vaporized fraction from the liquid fraction of the retentate in a drum separator, to recycle the vaporized fraction to debutanizer D at a tray which is higher than that at which the liquid fraction is admitted and optionally higher than that from which lateral extraction is effected.

Pervaporation unit PV produces a permeate via line 7 which is in the vapor phase at a pressure which is generally below atmospheric pressure, preferably between 10 and 500 mbar, mainly constituted by alcohols (ethanol, TBA). The composition of the permeate is a function of the operating conditions of the process (flow rate and composition of the phase extracted as a side stream from debutanizer D, and the surface area of the membrane used). The permeate most frequently contains more than 90% by weight of alcohols. It is then condensed in exchanger E4, then brought by pump P3 to a pressure above atmospheric pressure which is preferably sufficient to be recycled to the reaction section, and recovered via line 8 from which it is preferably recycled to the reaction section.

ADVANTAGES OF THE PROCESS

The process of the present invention has the main advantage of great simplicity as it can produce purified ETBE using a single permeation unlit in addition to the debutanizer present in all the processes previously described for the synthesis of ETBE. All the other processes previously described for purifying ETBE require the use of at least two columns in addition to the debutanizer. The process of the present invention is thus particularly economical as regards investment.

In addition, the preferred use of permeation in addition to the debutanizer means that a separation process is used which consumes far less energy than distillation, means that the process of the present invention is particularly economical as regards energy.

The process of the present invention has a further advantage of not allowing the impurities (TBA, $C_3$, $C_5$, water, DEE, E2BE) to accumulate in the ethanol/ETBE/$C_4$ mixture to be separated, since these are eliminated with the different products from the process ($C_4$/ethanol mixture overhead from the debutanizer, ETBE from the bottom of the debutanizer and permeate from permeation unit PV). The process of the present invention does not therefore require a purge, contrary to the processes described in French patents FR-B-2 672 048 and FR-B-2 673 624.

Finally, the use in the process of the present invention of a specific membrane which is selectively permeable not only to ethanol but also to TBA, means that these products can be recycled to the reaction section and, because of the recycle of a major portion of the TBA formed in the reaction section, conversion of isobutene to TBA is considerably reduced, as mentioned above, further increasing conversion of isobutene to ETBE.

In a variation to the process of the invention, debutaniser D is replaced by a catalytic or reactive column D', meaning that the conversion rates of isobutene can be increased and/or the excess of ethanol used can be reduced. The effluents from column D' will have analogous compositions to those in debutanizer D simply with generally reduced ethanol contents.

The process for the purification of ETBE from a ETBE/ethanol/hydrocarbon mixture, as described above, can readily be integrated into a process for the synthesis of ETBE from ethanol and isobutene contained in a $C_4$ cut which can, for example, be sent from a steam cracking, catalytic cracking or butane dehydrogenation unit.

Such a process for the synthesis of ETBE will be described below with reference to FIG. 2. In FIG. 2, the various apparatus (pumps, heat exchangers, pressure reduction valves, drums . . . ) which are required for the different steps of the process to be operated have not been shown.

The $C_4$ cut containing isobutene and minor amounts of $C_3$ and $C_5$ is supplied via line 20 as a liquid. The ethanol which is added for the reaction is supplied via line 21 in the liquid phase. The water/ethanol azeotrope produced by section LD, which washes raffinate $C_4$ from debutanizer D (or D'), is recycled as a liquid via line 24. The condensed permeate produced by permeation zone PV is recycled as a liquid via line 8. These fluids are mixed then introduced into reaction section R via line 22.

A mixture constituted by ETBE, non reactive and unreacted $C_4$ hydrocarbons, excess unreacted ethanol and the various impurities mentioned above (TBA, water, $C_3$, $C_5$, DEE, E2BE), is produced via line 1 from reaction section R. This mixture feeds the debutanizer D.

Purified ETBE is recovered from the bottom of debutanizer D (or D') via line 9, with traces of other ethers (DEE, E2BE) and hydrocarbons, water and a variable proportion, generally 1% to 5% by weight, of ethanol, is recovered overhead. This raffinate, once liquefied, is introduced into water washing section LD via line 3.

This water washing section LD is in fact constituted by a water washing step per se producing practically ethanol-free hydrocarbons via line 23, also a water/ethanol mixture, and a distillation step for this mixture which produces water from the bottom which is recycled to the water washing section and an azeotropic water/ethanol mixture containing about 5% by weight of water is produced overhead and recycled via line 24 to reaction section R.

A phase is extracted as a side stream from debutanizer D (or D') and supplied to permeation zone PV via line 5.

This permeation zone PV produces a retentate which is depleted in alcohol (ethanol, TBA) which is recycled via line 6 to debutanizer D (or D'), and a permeate which is mainly constituted by alcohols (ethanol, TBA) which is recycled after condensing to reaction section R, via line 8.

When debutanizer D is replaced by a catalytic or reactive column D', it can be advantageous to recycle the permeate at least in part via line 25 to the catalytic or reactive distillation column D'. The permeate is mainly constituted by alcohols and is produced by permeation zone PV.

It may also be of advantage to recycle the azeotropic ethanol/water mixture produced by the water washing section LD at least in part, via line 26 to the catalytic or reactive distillation zone D'.

The following examples illustrate the invention.

EXAMPLE 1

A solution of a copolymer of NVP and DMAEMA was deposited on a porous polyacrylonitrile (PAN) layer which was itself supported by a sheet of non woven polyester. The molar ratio of NVP and DMAEMA monomers in the copolymer was 1:1. The copolymer solution was constituted by a mixture of 10% by weight of copolymer in water. After deposition on the porous support, the solution was evaporated for 2 minutes at 90° C. The membrane obtained was then heat treated for 30 min at 125° C.

A pervaporation test was carried out with this membrane using a mixture constituted by 25% by weight of ethanol and 75% by weight of ETBE, at a temperature of 95° C. The pressure downstream of the membrane was 20 mbar. The permeate was condensed at a temperature of 0° C. A permeate stream of 6.2 kg.h$^{-1}$.m$^{-2}$ was obtained. The ethanol concentration in the permeate was 94.7% by weight.

EXAMPLE 2

A solution of equal weights of water and ethanol containing 7% by weight of DMAEMA was deposited on an identical support to that used in Example 1. After evaporating the solution for 2 min at 80° C., the membrane obtained was heat treated for 15 min at 150° C. The selective DMAEMA layer was 3 μm thick.

A pervaporation test was carried out with this membrane using a mixture constituted by 20% by weight of ethanol and 80% by weight of ETBE, at 60° C. The pressure downstream of the membrane was 6 mbar and the permeate was condensed in a trap immersed in a mixture of ethanol and dry ice. A permeate stream of 0.92 kg.h$^{-1}$.m$^{-2}$ was obtained. The ethanol concentration in the permeate was 98.2% by weight.

EXAMPLE 3

A solution of a copolymer of NVP and DMAEMA was deposited on a porous polyfluorovinylidene (PVDF) layer which was itself supported by a sheet of non woven polyphenylene sulphide (PPS). The amine group of the DMAEMA was quaternized by diethyl sulphate. The molar ratio of NVP to quaternized DMAEMA was 3:2. The solution was constituted by 4.5% by weight of copolymer in water. After evaporation for 2 minutes at 80° C., the membrane obtained was heat treated for 10 min at 115° C. then 5 min at 150° C.

A pervaporation test was carried out with this membrane using a mixture constituted by 20% by weight of ethanol and 80% by weight of toluene at 80° C. The pressure downstream of the membrane was 10 mbar. The permeate was condensed at a temperature of 0° C. A permeate stream of 2.5 kg.h$^{-1}$.m$^{-2}$ was obtained. The ethanol concentration in the permeate was 98.8% by weight.

EXAMPLE 4

A solution of 5% by weight of a terpolymer of NVCL, NVP and DMAEMA in water was deposited on a support identical to that of Example 1. The amine group of the DMAEMA was quaternized by monochloromethane. The molar composition of the terpolymer of monomers of NVCL, NVP and DMAEMA respectively was 0.3:0.3:0.4. After evaporation of the solution for 30 sec at 95° C., the membrane obtained was heat treated for 10 min at 120° C. then 8 min at 145° C.

A pervaporation test was carried out with this membrane using a mixture constituted by 20% by weight of ethanol and 80% by weight of n-heptane at 50° C. The pressure downstream of the membrane was 5 mbar. The permeate was condensed in a trap immersed in a mixture of ethanol and dry ice. A permeate stream of 1.8 kg.h$^{-1}$.m$^{-2}$ was obtained. The ethanol concentration in the permeate was 99.2% by weight.

A pervaporation test was then carried out on a membrane prepared in the same way, using a mixture constituted by 5% by weight of methanol and 95% by weight of n-heptane at 55° C. The pressure downstream of the membrane was 5 mbar. The permeate was condensed in a trap immersed in a mixture of ethanol and dry ice. A permeate stream of 2.3 kg.h$^{-1}$.m$^{-2}$ was obtained. The ethanol concentration in the permeate was 99.8% by weight.

Finally, again using a membrane prepared in the same way, a pervaporation test was carried out using a mixture constituted by 10% by weight of 2-propanol and 90% by weight of n-heptane, under the same conditions. A permeate stream of 0.8 kg.h$^{-1}$.m$^{-2}$ was obtained. The 2-propanol concentration in the permeate was 92.7% by weight.

EXAMPLE 5

A membrane was formed using the procedure described in Example 1. A pervaporation test was carried out on this membrane using a mixture constituted by 0.1% by weight of water; 15.6% by weight of ethanol; 1.0% by weight of DEE; 5.3% by weight of TBA and 78.0% by weight of ETBE, at a temperature of 48° C. The pressure downstream of the membrane was 8 mbar. The permeate was condensed in a trap immersed in liquid nitrogen. A permeate stream of 0.12 kg.h$^{-1}$.m$^{-1}$ was obtained which had the following composition: water: 4.5% by weight, ethanol: 90.8% by weight, DEE: 0.3% by weight, TBA:2.3% by weight and ETBE: 2.1% by weight. The selectivity $\alpha_{i/j}$ of the membrane for compound i with respect to compound j was calculated using the formula:

$$\alpha_{i/j} = \frac{c'_i}{c_i} / \frac{c'_j}{c_j}$$

where $c'_i$ and $c'_j$ represent the respective concentrations by weight of compounds i and j in the permeate, $c_i$ and $c_j$ represent. the respective concentrations by weight of compounds i and j in the mixture upstream of the membrane. With this formula, the pervaporation experiment carried out means the following could be calculated:

$\alpha_{water/ETBE}=1671$ $\alpha_{ethanol/ETBE}=216$ $\alpha_{TBA/ETBE}=16$ $\alpha_{DEE/ETBE}=11$ This example illustrates the fact that the membrane is selectively permeable not only to ethanol but also to other oxygenated compounds, in particular TBA in the presence of mixtures of these products with ETBE.

EXAMPLE 6

A mixture of $C_4$/ethanol/ETBE, representing an effluent from a reaction section in an etherification process, was separated to obtain the $C_4$ cut overhead of debutanizer D containing less than 1 ppm by weight of ETBE, and ETBE from the bottom of the debutanizer containing less than 0.1% by weight of residual alcohols.

Pervaporation unit PV produced a liquid retentate RETE which was returned by means of pump P2 to tray 58 of debutanizer D, after being brought to a temperature of 119.0° C. in exchanger E3. The flow rate and composition of retentate RETE are shown in Table 1.

Pervaporation unit PV produced a vapour phase PERMEAT at a pressure of 20 mbar which was condensed in cryogenic condenser E4, pumped by pump P3 and recovered. The flow rate and composition of this permeate, PERMEAT, are shown in Table 1.

TABLE 1

| BODY (weight %) | ALIMENTATION | Material balance | | | | |
| --- | --- | --- | --- | --- | --- | --- |
| | | HC | EXTR | RETE | PERMEAT | ETHER |
| Hydrocarbons | 67.16 | 97.7 | 28.48 | 30.32 | 2.67 | 1.26 |
| Ethanol | 3.72 | 2.09 | 10.76 | 5.76 | 81.36 | 0.03 |
| ETBE | 28.63 | <1 ppm | 55.21 | 58.75 | 5.18 | 98.60 |
| TBA | 0.30 | 29 ppm | 4.58 | 4.20 | 9.91 | 0.05 |
| DEE | 0.05 | 64 ppm | 0.97 | 0.97 | 0.88 | 0.06 |
| Water | 0.14 | 0.20 | <1 ppm | <1 ppm | 3 ppm | <1 ppm |
| Flow rate, g · h$^{-1}$ | 6000.0 | 4097.0 | 2547.0 | 2378.0 | 169.0 | 1734.0 |

The composition and the flow rate of the mixture to be separated, SUPPLY, are shown in Table 1.

Debutanizer D was constituted by a stainless steel column with an internal diameter of 100 mm, containing 70 perforated baffle trays spaced 5 cm apart.

This was thermally insulated to prevent wall loss and provided with an electrically heated boiler R, a cold water condenser E1 and a reflux drum B.

The debutanizer trays were numbered in increasing order from 1 at the top towards the bottom.

Debutanizer D was operated at a pressure of 0.8 bar, measured at reflux drum B. The temperature in column D ranged between 161.2° C. at the bottom and 67.5° C. at the top. The distillate obtained overhead from debutaniser D was condensed then undercooled: the temperature in reflux drum B was thus held at 50° C.

The mixture for separation, SUPPLY, was introduced in the liquid phase into debutanizer D at tray 40 at a temperature of 75.5° C.

Mixture HC of distilled hydrocarbons was extracted as a liquid phase from reflux drum B. The flow rate and the composition of this mixture HC are shown in Table 1. The residual liquid fraction obtained from drum B, with the same composition as mixture HC, was sent as a reflux to the top of debutanizer D at a flow rate of 3300 g.h$^{-1}$, representing a weight reflux ratio with respect to SUPPLY of 0.55.

A purified liquid ETBE phase, ETHER, was recovered from the debutanizer. The flow rate and composition of producer ETHER obtained are shown in Table 1.

A liquid phase, EXTR, was extracted from tray 54 of debutanizer D, at a temperature of 118.4° C. The flow rate and composition of this liquid phase are given in Table 1.

The liquid phase was then cooled to a temperature of 90° C. in a cold water condenser E2. It was then sent to pervaporation unit PV. This unit was constituted by a cell with an effective permeation surface area of 0.1 m$^2$. It was provided with a membrane formed using the method described in Example 1.

This example clearly shows the advantages of the process of the invention, namely that ETBE can be produced with a total alcohol content (ethanol+TBA) of less than 0.1% by weight, and also that 93%, i.e., almost all of the TBA produced by the reaction section, is found in PERMEAT and can thus be recycled to the reaction section, thus limiting the conversion of isobutene to TBA. It should also be noted that the quantity of ETBE recovered in PERMEAT which can thus be recycled to the reaction section is negligible since this is only 0.51% of the ETBE produced. Recycling of such a minimal quantity of ETBE to the reaction section does not disturb the operation in this section.

I claim:

1. A process for the separation of a mixture of ethyl tertio-butyl ether and ethanol wherein said mixture contains $C_4$ hydrocarbons said process comprising the following steps:

a) introducing the mixture to be separated into a distillation zone termed a debutanizing zone, from which substantially all of the $C_4$ hydrocarbons are recovered as overhead effluent and purified ethyl tertio-butyl ether is recovered as bottom effluent;

b) removing at least one phase selected from the group consisting of a liquid phase, a vapor phase and a mixed liquid-vapor phase as a side stream from said distillation zone and sending it to a permeation zone from which a retentate is recycled to the distillation zone and a permeate comprising ethanol is produced, wherein the phase to be sent to the permeation zone is removed from a tray in said distillation zone which substantially corresponds to the maximum concentration of the ethanol, and said permeation zone being provided with a separation membrane comprising at least one selective layer constituted by a dense film of at least one polymer selected from the group consisting of homopolymers of dimethylaminoethyl methacrylate, copolymers of dimethylaminoethyl methacrylate and N-vinylcaprolactam, copolymers of dimethylaminoethyl methacrylate and N-vinyl pyrrolidone and terpolymers of dimethylaminoethyl methacrylate, N-vinyl caprolactam and N-vinyl pyrrolidone.

2. A process according to claim 1 wherein the mixture to be separated is supplied from an etherification reaction zone wherein isobutene is reacted with ethanol.

3. A process according to claim 1 wherein the ethyl tertio-butyl ether-ethanol mixture to be separated can optionally contain, in addition to a proportion of $C_4$ hydrocarbons, up to 1% by weight of water, up to 1% by weight of tertiary butyl alcohol, up to 1% by weight of diethyl ether, up to 1% by weight of ethyl 2-butyl ether, up to 5% by weight of $C_5$ hydrocarbons and up to 5% by weight of $C_3$ hyrocarbons.

4. A process according to claim 3, wherein in step a), the overhead effluent from the distillation zone further comprises a major portion of the $C_3$ hydrocarbons, a major portion of the water, a fraction of the ethanol and the $C_5$ hydrocarbons from the mixture to be separated and is substantially free of ethyl tertio-butyl ether, ethyl-2-butyl ether, tertiary butyl alcohol and diethyl ether; and the bottom effluent from said distillation zone comprises, in addition to the purified ethyl tertio-butyl ether, a major portion of the ethyl 2-butyl ether, a portion of the diethyl ether, a fraction of the $C_5$ hydrocarbons and less than 1% by weight of ethanol and tertiary butyl alcohol; and the permeate leaving the permeation zone consists mainly of ethanol and tertiary butyl alcohol.

5. A process according to claim 1 wherein the purified ethyl tertio-butyl ether recovered from the bottom of the distillation zone contains less than 0.1% by weight of ethanol and tertiary butyl alcohol.

6. A process according to claim 1 wherein the phase removed from the distillation zone is a liquid phase and the permeation consists of pervaporation.

7. A process according to claim 1 wherein the phase extracted from the distillation zone is a vapor or mixed phase and the permeation consists of vapor permeation.

8. A process according to claim 1 wherein in step a), the distillation zone operates at a pressure that is greater than atmospheric pressure, at a bottom temperature of 70° C. to 200° C., at a top temperature of 30° C. to 100° C., the mixture to be separated is introduced into said distillation zone at a bubble point at the corresponding pressure to a tray containing the composition which is close to the composition of said mixture; and in that, in step b), the phase to be sent to the permeation zone is heated to a temperature of 50° C. to 120° C. and introduced into the permeation zone which produces a retentate which is recycled to the distillation zone at the bubble point at the corresponding pressure to the tray at which the composition of the liquid is as close to the composition of said retentate; and a vapor phase permeate is produced at a pressure which is lower than atmospheric pressure.

9. A process according to claim 8, wherein the retentate from the permeation zone is at least partially vaporized before being recycled to the distillation zone.

10. A process according to claim 8, wherein the retentate from the permeation zone is partially vaporized, a liquid fraction is separated and recycled to the distillation zone to a lower tray than that from which the side stream is removed and a vapor fraction is separated which is recycled to the distillation zone to a higher tray than the recycle tray for said liquid fraction.

11. The process of claim 8 wherein said greater than atmospheric pressure is between 5 and 15 bar; and said lower than atmospheric pressure is between 20 and 500 mbar.

12. A process according to claim 1 wherein, in step a), the overhead vapor effluent from the distillation zone is condensed and a portion of the condensate is sent as a reflux to the top of the distillation zone.

13. A process for the synthesis of ethyl tertio-butyl ether from ethanol and from isobutene contained in a $C_4$ cut and its separation which comprises the following steps:

1) mixing a $C_4$ cut, ethanol, a water-ethanol azeotrope from a washing section for a raffinate from a distillation zone D or catalytic or reactive distillation zone D' and a condensed permeate from a permeation zone, and introducing the mixture formed into a reaction section R, which operates under conditions for etherification of isobutene and ethanol;

2) supplying the zone D or D' with effluent from reaction zone R which comprises the ethyl tertio-butyl ether product, non reactive or unreacted $C_4$ hydrocarbons, excess ethanol and impurities comprising tertiary butyl alcohol, water, $C_3$ and $C_5$ hydrocarbons, diethyl ether and ethyl 2-butyl ether; recovering from the bottom of zone D or D' as bottom effluent, purified ethyl tertio-butyl ether which contains traces of diethyl ether and ethyl 2-butyl ether, and recovering an overhead effluent containing hydrocarbons, water and a fraction of the ethanols, and extracting a phase from zone D or D' as a side stream from a tray in said distillation zone D or D' which corresponds substantially to the maximum concentration of the ethanol and sending it to a permeation zone PV; said permeation zone PV being provided with a separation membrane comprising at least one selective layer constituted by a dense film of at least one polymer selected from the group consisting of homopolymers of dimethylaminoethyl methacrylate, copolymers of dimethylaminoethyl methacrylate and N-vinylcaprolactam, copolymers of dimethylaminoethyl methacrylate and N-vinyl pyrrolidone and terpolymers of dimethylaminoethyl methacrylate, N-vinyl caprolactam and N-vinyl pyrrolidone;

3) carrying out permeation on said phase, producing a retentate which is depleted in ethanol and tertiary butyl-alcohol which is recycled to the zone D or D', and a permeate comprising ethanol and tertiary butyl alcohol which is recycled to the reaction zone R or to said catalytic or reactive distillation zone D';

4) sending the overhead effluent vapor from the zone D or D', following condensation to a water washing section LD, which produces an effluent constituted by hydrocarbons which are substantially free of ethanol and a water-ethanol mixture which is separated by distillation into a water bottom product which is recycled to the washing section and an overhead azeotropic water-ethanol mixture containing about 5% by weight of water, which is recycled to the reaction section R or to said catalytic or reactive distillation zone D'.

14. The process of claim 13 wherein distillation zone D is employed.

15. The process of claim 13 wherein catalytic or reactive distillation zone D' is employed.

16. A process according to claim 15 wherein at least a portion of the permeate produced by the permeation zone of step 3) is recycled to said catalytic or reactive distillation zone D'.

17. A process according to claim 15 wherein at least a portion of the azeotropic water-ethanol mixture produced by the washing-distillation zone in step 4) is recycled to said catalytic or reactive distillation zone D'.

* * * * *